(12) United States Patent
Gibson et al.

(10) Patent No.: US 7,226,460 B2
(45) Date of Patent: Jun. 5, 2007

(54) SURGICAL INSTRUMENT ATTACHMENT SYSTEM

(75) Inventors: Roger A. Gibson, Fullerton, CA (US); Dana J. Landry, Sturbridge, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 231 days.

(21) Appl. No.: 10/909,651

(22) Filed: Aug. 2, 2004

(65) Prior Publication Data
US 2006/0025792 A1    Feb. 2, 2006

(51) Int. Cl.
*A61B 17/00* (2006.01)
(52) U.S. Cl. ..................................................... 606/180
(58) Field of Classification Search ............... 606/180, 606/170, 172, 174, 171, 159; 604/22
See application file for complete search history.

(56) References Cited

U.S. PATENT DOCUMENTS

| | | | | |
|---|---|---|---|---|
| 2,807,473 A | 9/1957 | Kiehne | .......................... | 279/82 |
| 5,217,479 A * | 6/1993 | Shuler | .......................... | 606/180 |
| 5,222,956 A | 6/1993 | Waldron | ........................ | 606/80 |
| 5,364,395 A | 11/1994 | West | ................................ | 606/46 |
| 5,376,078 A | 12/1994 | Dinger et al. | ................. | 606/170 |
| 5,380,333 A | 1/1995 | Meloul et al. | .................. | 606/80 |
| 5,505,737 A | 4/1996 | Gosselin et al. | ............... | 606/79 |
| 5,601,583 A | 2/1997 | Donahue et al. | ............. | 606/170 |
| 5,782,795 A | 7/1998 | Bays | ........................... | 604/22 |
| 5,782,836 A | 7/1998 | Umber et al. | .................. | 606/79 |
| 5,792,167 A * | 8/1998 | Kablik et al. | ................ | 606/180 |
| 5,989,257 A | 11/1999 | Tidwell | ........................ | 606/79 |
| 6,033,408 A | 3/2000 | Gage et al. | .................... | 606/79 |
| 6,342,061 B1 | 1/2002 | Kauker | ......................... | 606/180 |
| 2004/0059363 A1 | 3/2004 | Alvarez | ....................... | 606/170 |

* cited by examiner

*Primary Examiner*—Kevin T. Truong
(74) *Attorney, Agent, or Firm*—St. Onge Steward Johnston & Reens LLC

(57) ABSTRACT

A surgical implement for use with a handpiece of a surgical instrument for performing a surgical treatment, comprises: an outer tube member including an outer hub and an outer tube extending longitudinally from the outer hub, the outer tube and the outer hub defining a longitudinal bore, the outer hub having a generally circular outer surface and including a circumferential locking groove and a key for releasable attachment of the outer tube member to the surgical instrument; and, an inner tube member including an inner hub and an inner tube extending longitudinally from the inner hub, the inner tube and the inner hub defining a longitudinal bore, the inner tube configured to insert within the longitudinal bore of the outer tube member and including an end effect portion disposed adjacent to a distal end of the inner tube, the inner hub having a generally circular outer surface and including a plurality of bosses radially formed on the outer surface thereof for releasably connecting the inner tube member to an actuator of the surgical instrument for performing the surgical treatment. A surgical instrument having a coupling for releasable attachment of the surgical implement is also disclosed.

25 Claims, 4 Drawing Sheets

SURGICAL INSTRUMENT ATTACHMENT SYSTEM

FIELD OF THE INVENTION

The present invention relates to a surgical instrument, and more particularly, to a surgical implement and a surgical instrument with the surgical implement releasably attached thereto by a coupling means.

BACKGROUND OF THE INVENTION

An endoscopic, arthroscopic, and other minimally-invasive surgeries are well known surgical procedures to perform various surgical tasks. During these surgical procedures, only a small portions of the patient's tissue or internal organs are exposed to an open environment through small incisions made in the patient body.

The ability to perform these minimally invasive surgeries has been enhanced by the development of powered surgical instruments with a wide variety of different structures and configurations. A surgical instrument of this type generally includes a handpiece with an elongated cylindrical body containing a motor therein, and a surgical probe or a surgical implement attached to the handpiece. A distal or front end of the handpiece is often provided with a coupling assembly for releasably attaching the surgical implement, such as edgers, resectors, planers, burrs, and the like. A mechanism for transmitting the rotation of the motor to the surgical implement is also provided within the handpiece.

The handpiece also typically has a suction valve and conduit for removing irrigating fluid and tissue and debris from the surgical site. For this, a suction pump is connected to the handpiece and provides the suction force for drawing the fluid and debris away from the surgical site.

SUMMARY OF THE INVENTION

The present invention is generally directed to a new surgical implement and a surgical instrument incorporating the surgical implement by a coupling means disposed at a distal end portion of the instrument handpiece, wherein the surgical implement can be easily and quickly attached to the handpiece for performing surgical treatments to a surgical site, as well as it can be quickly detached therefrom for further operations.

According to one aspect of the invention, a surgical implement for use with a handpiece of a surgical instrument for performing a surgical treatment to a human or animal body, comprises an outer tube member and an inner tube member. The outer tube member includes an outer hub, and an outer tube which extends longitudinally from the outer hub, the outer tube and the outer hub defining a longitudinal bore, the outer hub including a circumferentially extending locking groove and an engaging element disposed at an outer surface of the outer hub for releasable attachment of the outer tube member to the surgical instrument. The inner tube member includes an inner hub, and an inner tube which extends longitudinally from the inner hub, the inner tube and the inner hub defining a longitudinal bore, the inner tube configured to insert within the longitudinal bore of the outer tube member and including an end effect portion disposed adjacent to a distal end of the inner tube, the inner hub including a connection element radially extending from an outer circumference of the inner hub for releasable connection of the inner tube member to an actuator (e.g., a rotor) of the surgical instrument for performing a surgical treatment.

Preferably, the engaging element of the outer tube member comprises a key for engaging with a coupling of the surgical instrument. The connection element of the inner hub includes a plurality of (e.g., four) bosses equidistantly spaced apart and radially extending from the outer circumference of the inner hub.

According to another aspect of the invention, a surgical instrument for performing a surgical treatment comprises a surgical implement and a handpiece. The implement of the surgical instrument includes an elongate outer tube member and an elongate inner tube member, the outer tuber member defining a longitudinal bore, the outer tube member including a distal outer tube and a proximal outer hub, the outer hub having a circumferential locking groove and an engaging element at an outer circumference thereof, the inner tuber member defining another longitudinal bore, the inner tube member including a distal inner tube and a proximal inner hub, the inner hub having a connection element radially extending from an outer circumference of the inner hub, the inner tube of the inner tube member configured to slidably insert within the longitudinal bore of the outer tube member.

The handpiece of the surgical instrument includes an actuator (e.g., a rotor), and a coupling for attaching the surgical implement to the handpiece. The coupling of the handpiece includes a generally cylindrical coupler, the coupler having a longitudinal opening configured to receive a proximal portion of the surgical implement therein and at least one circumferential hole formed through the cylindrical coupler in a radial direction, the coupler further having a counterpart engaging element connectable with the engaging element of the outer hub for attachment of the surgical implement to the handpiece. The coupling of the handpiece further includes at least one locking ball slidably received within the circumferential hole of the coupler, and an outer slider having a longitudinal opening for receiving the coupler therein, the outer slider including a circumferential inner recess and being moveable along the coupler between a lock position where the locking ball is pushed radially by the outer slider for engaging with the circumferential locking groove of the outer hub of the surgical implement for connection of the surgical implement to the coupling of the handpiece and an unlock position where the locking ball is at least partially retrieved into the circumferential recess of the outer slider for allowing detachment of the surgical implement from the coupling of the handpiece. A distal end of the rotor includes a counterpart connection element for connecting with the connection element of the inner hub of the surgical implement for performing a surgical treatment.

Preferably, the outer hub of the surgical implement further includes a key at an outer circumference of the outer hub and the coupler includes one or more distal grooves for receiving the key of the outer hub for secured connection of the surgical implement to the handpiece. The connection element of the inner hub includes a plurality of bosses equidistantly spaced apart and radially extending from the outer circumference of the inner hub, and the counterpart connection element of the rotor includes a plurality of longitudinally extending coupling grooves for receiving the bosses of the inner hub for the connection of the inner hub with the rotor. The coupling further includes a spring disposed between the coupler and the outer slider, which is preferably biased to push the outer slider to the lock position. The surgical instrument preferably includes a suction member configured to draw irrigating fluid and tissue debris via the longitudinal bore of the inner tube member.

BRIEF DESCRIPTION OF THE DRAWINGS

The above-described and other features and advantages of the present invention will become more apparent by describing in details preferred embodiments of the invention with reference to the accompanied drawings in which.

DETAILED DESCRIPTION OF THE DRAWINGS

Figure 1:
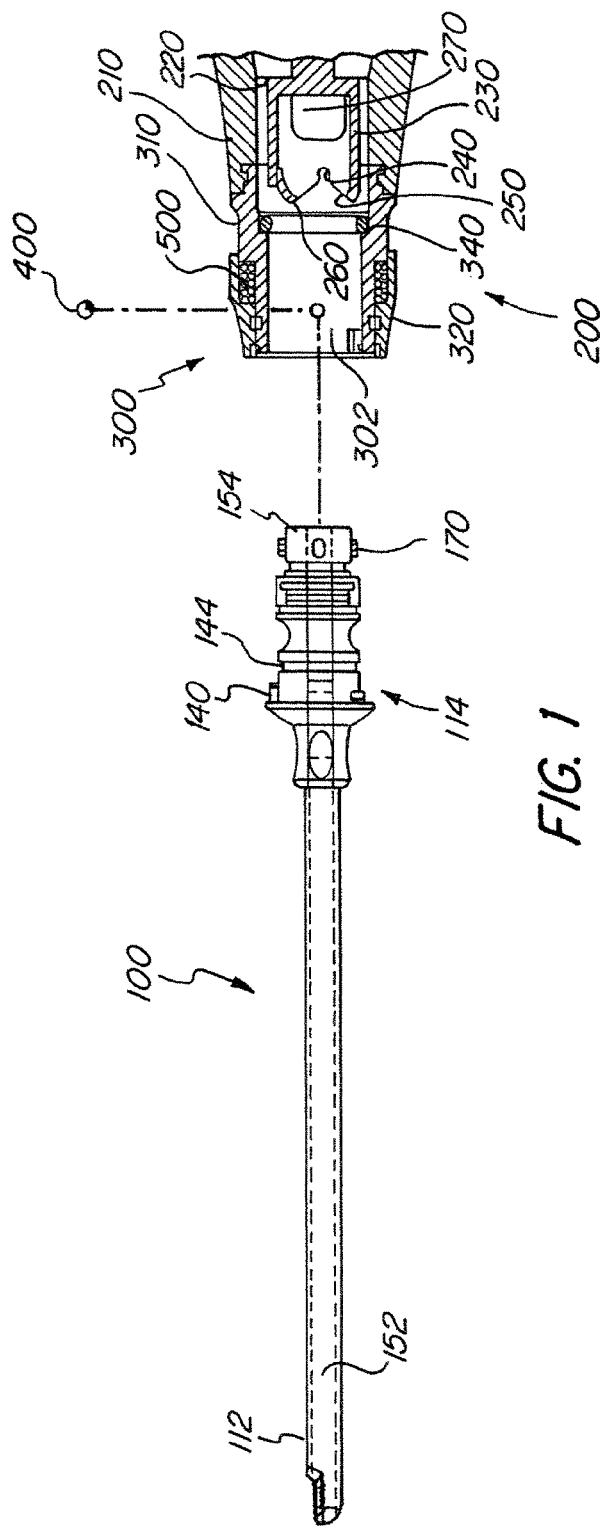
FIG. 1 is a partially sectional view illustrating a surgical instrument with a surgical implement for attaching to a coupling of the surgical instrument, constructed according to the principles of the present invention.

Referring to FIG. 1, a surgical instrument of the invention includes a surgical implement 100, and a surgical handpiece 200 having a coupling 300 disposed at a distal portion of the handpiece 200.

Figure 2:
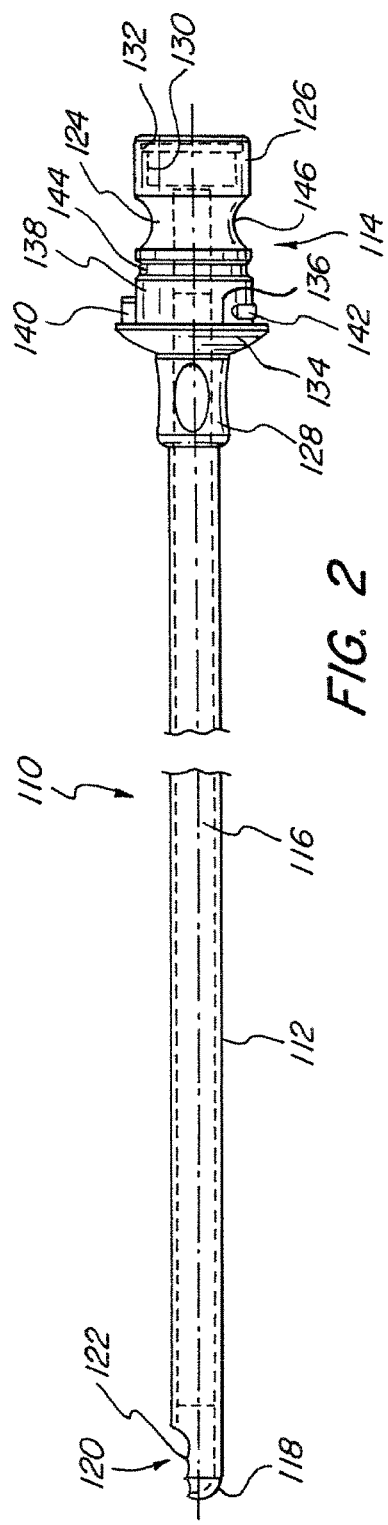
FIG. 2 is a side view illustrating the outer tube member of the surgical implement of FIG. 1.
Figure 3:
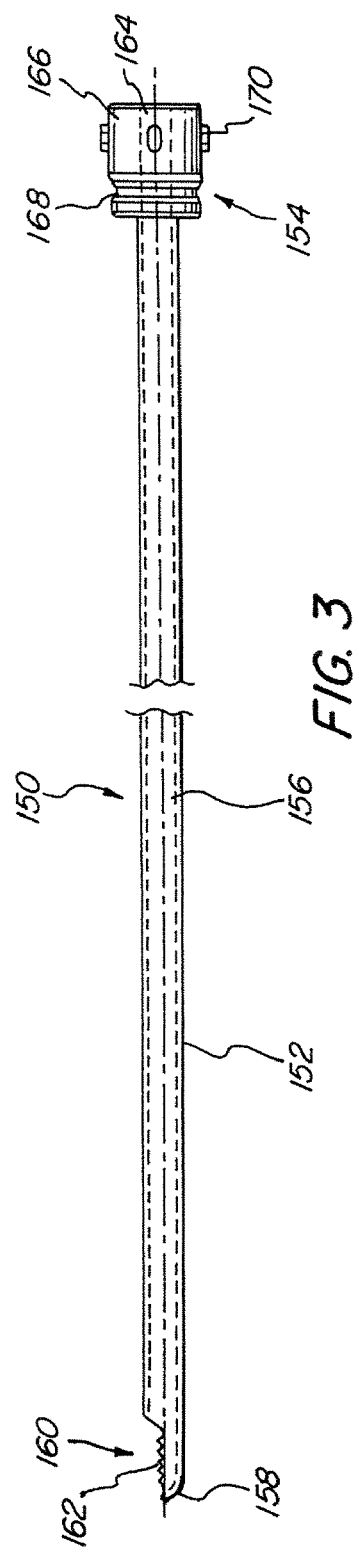
FIG. 3 is a side view illustrating the inner tube member of the surgical implement of FIG. 1.

Referring to FIGS. 1–3, the surgical implement 100 includes an outer tube member 110, and an inner tube member 150 which is inserted along a longitudinal bore of the outer tube member 110 when assembled as shown in FIG. 1 for certain surgical treatment procedures described above.

The outer tube member 110 consists generally of an elongate outer tube 112 and an outer hub 114 axially connected to each other. The outer tube 112 is formed of a generally circular thin tube configured to insert within an endoscopic or arthroscopic surgery site (not shown) of a human or animal body through a small opening. The outer tube 112 includes a longitudinal bore 116 along the length, which is open to the proximal end for receiving the inner tube member 150 within the bore 116 through the proximal end. According to one preferred embodiment, the distal end portion of the outer tube 112 has a nose portion 118 with a partially round tip and a lateral aperture or window 120 formed at a lateral side adjacent to the nose portion 118 for performing a surgical treatment therethrough. The tube portion at the window 120 may include a plurality of teeth 122 depending on the particular designs of the surgical implement 110. According to alternate embodiments, the window 120 may have a different configuration and be formed at locations other than the distal end of the outer tube 112 for performing certain surgical treatments as needed.

The outer hub 114 has a generally cylindrical shape with a longitudinal bore 124 formed axially therethrough between a proximal portion 126 and a distal portion 128. The distal end of the longitudinal bore 124 of the outer hub 114 receives and tightly fixes thereto a proximal end portion of the outer tube 112, and the longitudinal bores 124 and 116 of the outer hub 114 and the outer tube 112 communicate with each other. The proximal portion 126 of the outer hub 114 includes a counter bore portion 130 (i.e., a stepped bore) extending distally along the longitudinal axis from the proximal end surface of the proximal portion 126. The proximal portion 126 of the outer hub 114 may further include another counterbore portion 132 coaxially extending at the proximal end of the stepped bore 130. Next to the distal portion 128, a conical collar 134 is provided with a rear face 136 formed at a proximal end thereof.

The outer hub 114 includes an interim portion 138 disposed between the proximal portion 126 and the distal portion 128, which provides at an outer circumference of the interim portion 138 a key 140 and a pin 142 projecting outwardly from corresponding receiving grooves or holes formed at the outer surface of the interim portion 138. The key 140 has a rectangular, circular, or elliptic shape. Beneath the pin 142, a compression spring (not shown) may be provided within the pin hole to bias the pin 142 outwardly. The interim portion 138 includes a circumferential locking groove 144 for receiving locking balls of the coupling 300 as will be described herein below. Utilizing the key 140 (and the pin 142) and the locking groove 144, the outer tube member 110 is to be securely but releasably attached to the coupling 300 as will be also described herein below. In addition, in order to remove excessive material and make the implement lighter, the interim portion 138 may include another circumferential groove 146 formed there-around.

Referring to FIGS. 1 and 3, the inner tube member 150 consists generally of an elongate inner tube 152 and an inner hub 154 axially connected to each other. The inner tube 152 is formed of a generally circular thin tube configured to insert within the longitudinal bores 116 and 124 of the outer tube member 110 for a surgical treatment. The inner tube 152 includes an inner longitudinal bore 156 which is open to the proximal end. According to one preferred embodiment, the distal end portion of the inner tube 152 has a nose portion 158 with a partially round tip and a lateral aperture or window 160 formed at a lateral side adjacent to the nose portion 158 for performing a surgical treatment therewith. The tube portion at the window 160 may include a plurality of teeth 162 depending on the particular designs of the surgical implement 110. According to alternate embodiments, the window 160 may have a different configuration and be formed at locations other than the distal end of the inner tube 152 for performing certain surgical treatments as needed. According to still other alternate embodiments, the distal end portion of the inner tube 152 may not include the window 160, and instead, it may have a burring head (not shown) or other treatment member known in the art, for example, see FIG. 7 of U.S. Pat. No. 5,364,395, and FIGS. 2–4 of U.S. Pat. No. 6,251,120, etc. In any of the applicable designs, the distal window 160 (or other distal treatment member such as a burring head) of the inner tube 152 is configured to locate at a corresponding position to the window 120 of the outer tube 112 upon assembly of the surgical implement 100 for performing the surgical procedures.

The inner hub 154 has a generally cylindrical shape with a longitudinal bore 164 formed axially therethrough between a proximal portion 166 and a distal portion 168. The distal end of the longitudinal bore 164 of the inner hub 154 receives and tightly fixes thereto a proximal end portion of the inner tube 152, and the longitudinal bores 164 and 156 of the inner hub 154 and the inner tube 152 communicate with each other. These bores 156 and 164 can be used as a conduit for drawing and discharging the irrigating fluid and tissue debris from the surgical site by a suction pump or suction devices (not shown) attached to the handpiece 200 of the surgical instrument of the invention. A plurality of (e.g., four) bosses 170 are disposed along a circumference of the proximal portion 166 of the inner hub 154. The bosses 170 are of a circular or elliptic configuration and spaced apart with one another by an equal distance. The distal portion 168 of the inner hub 154 has a generally cylindrical shape with the distal end portion thereof configured to be slidingly and rotatably received within the counter bores 130 and 132 of the outer hub 114 as shown in FIG. 1.

As shown in FIG. 1, upon assembly of the inner tube member 150 into the outer tube member 110, the inner tube 152 and the distal portion 168 of the inner tube member 150 is slidably (and rotatably) received within the longitudinal bores 116 and 124 of the outer tube member 110 with the outer and inner tubes 112 and 152 juxtaposingly positioned. However, the proximal portion 166 of the inner hub 154 is projected outwardly and the bosses 170 are exposed to the outside environment.

It is noted that the outer tube member 110 and the inner tube member 150 (including the hubs 114 and 154) are preferably formed of stainless steel, metal, or other suitable material to be used for surgical implements, which is preferably reusable for later surgical operations after appropriate sterilization.

However, provision for disposable type implement is also contemplated by the present invention. For this type of implements, the outer and inner tube members 110 and 150 may be formed of light-weight metal, alloy, or a plastic material such as engineering plastic. Alternatively, the tubes 112 and 152 can be formed of stainless steel, while forming the hubs 114 and 154 from a plastic material.

Referring now to FIGS. 1, and 4–6, further features of the present invention are described herein in detail.

As shown in FIG. 1, the handpiece 200 includes the coupling 300 affixed at a distal end of a handpiece housing 210, and a rotor 220 rotatably disposed within the housing 210. A motor or rotation actuator (not shown) is disposed within the housing 210 for providing a rotation force to the rotor 220, and other components (not shown) of the surgical instrument are also provided in association with the handpiece 200.

The distal portion of the rotor 220 includes a rotor hub 230 with a hollow interior opening adapted for slidably receiving the proximal end portion of the inner hub 154 and with a plurality of (e.g., four) coupling grooves 240 formed at the distal end thereof. The coupling grooves 240 are spaced apart with one another by an equal distance, and correspond to the intervals of the bosses 170 of the inner hub 154 for connection thereto upon assembly of the surgical implement 100 onto the coupling 300, thereby enabling rotation of the inner tube member 150 by the rotor 220. The distal end of the rotor hub 230 includes a plurality of guide slops 250 extending diagonally outward from the coupling grooves 240 and defining a plurality of (e.g., four apex points 260 at a distal endmost portion of the rotor hub 230. With the guide slops 250 formed adjacent to the coupling grooves 240, the bosses 170 formed on the inner hub 154 is automatically guided into the coupling grooves 240 while the inner hub 154 is adjusting its rotational orientation when the assembled implement 100 is inserted (and thereby assembled) within the longitudinal opening 302 of the coupling 300. A lateral suction opening 270 is provided at the housing 210 or at the hollow rotor hub 230 in fluid communication with the longitudinal bores 156 and 164 of the inner tube member 150 for drawing and discharging the irrigating fluid and tissue debris of the surgical site by a suction pump (not shown) coupled with the handpiece 200.

Referring to FIGS. 1 and 4–6, the coupling 300 includes a cylindrical coupler 310 and a outer slider 320 coupled with each other for providing a quick releasable attachment of the implement 100 to the coupling 300.

Figure 4:
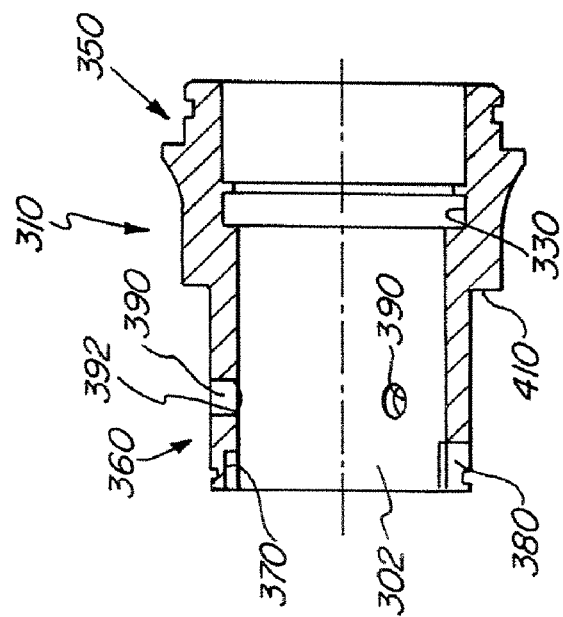
FIG. 4 is a side sectional view illustrating the coupler of the surgical instrument of FIG. 1.
Figure 5:
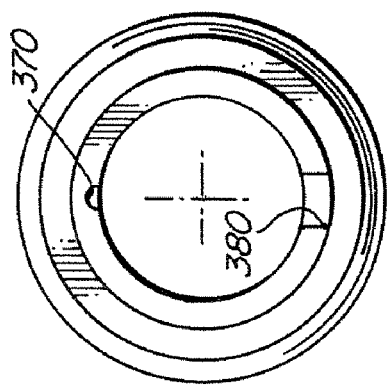
FIG. 5 is a front view shown from the distal end of the coupler of the surgical instrument of FIG. 1.

As particularly shown in FIG. 4, the coupler 310 has a generally cylindrical shape including a longitudinal interior opening 302 extending throughout the length with an annular groove 330 formed at a intermediate portion thereof for fixedly receiving an O-ring 340 (FIG. 1) therein, which is in turn to be in contact with the outer surface of the proximal portion 126 of the outer hub 114 for providing a sealing effect when the implement 100 is assembled into the coupling 300. This sealing arrangement can facilitate effective suction of the irrigating fluid by a suction pump as described above.

A proximal end portion 350 of the coupler 310 is configured to securely connect with the housing 210 of the handpiece 200. A distal end portion 360 includes at least one (e.g., two) key hole 380 for receiving the rectangular key 140 of the outer hub 114 in order to prevent the outer hub 114 (and the outer tube 112) from rotating upon rotation of the rotor 220. When the distal end portion 360 includes, for example, two radially-opposing holes 380 spaced 180° apart from each other at its top and bottom locations, the implement 100 can be inserted either in the up or down position upon the surgeon's selection to meet the particular surgical circumstances. The distal end portion 360 may further include a pin groove 370 for receiving the pin 142 of the outer hub 114.

A plurality of (e.g., two to four) circumferential radial holes 390 are formed along a circumference of the coupler 310 proximally to the pin holes 370 and the key holes 380. The circumferential holes 390 are configured to receive a plurality of (e.g., two to four) locking balls 400 (FIG. 1) therein, and include an annular seat 392 in order to prevent the locking balls 400 from slipping into the central opening 302 of the coupler 310. An outer shoulder 410 is provided at an intermediate portion of the coupler 310 to abut a proximal end of a compression spring 500 to be placed around the intermediate portion of the coupler 310 as shown in FIG. 1.

Figure 6:
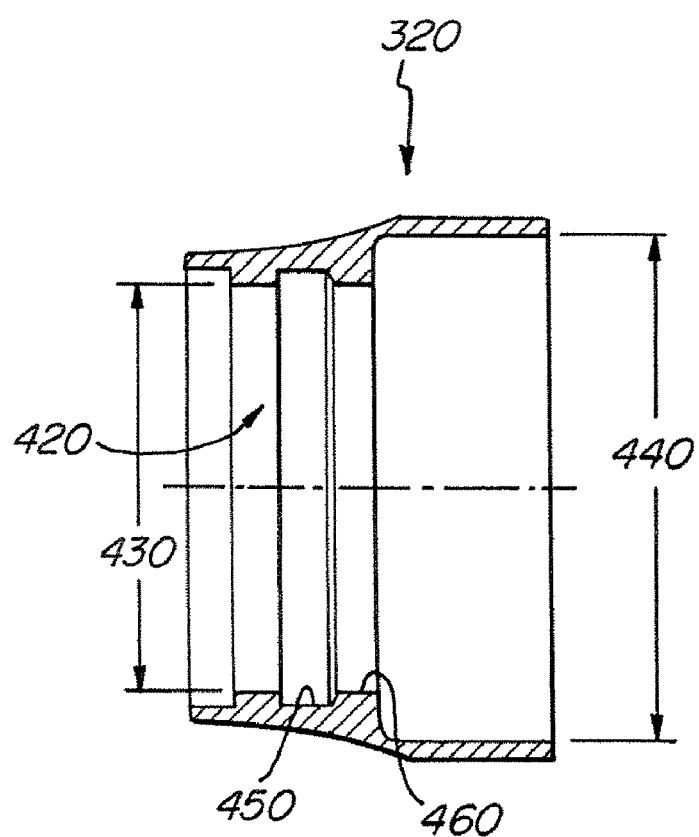
FIG. 6 is a side sectional view illustrating the outer slide of the surgical instrument of FIG. 1, which is to be slidingly coupled with the coupler for releasable attachment of the surgical implement to the handpiece of the surgical instrument.

Referring to FIGS. 1 and 6, the outer slider 320 of the coupling 300 has a generally cylindrical shape, and includes an inner axial opening 420 formed there-through with a proximal, first inner diameter 430 for slidably receiving the distal portion 360 of the coupler 310 and a distal, second inner diameter 440 for receiving the compression spring 500 therein. An annular inner groove or recess 450 is formed at an intermediate portion of the opening 420 for receiving the locking balls 400 therein when the outer slider 320 is pulled back (i.e., an unlock position) in order to detach the assembled implement 100 from the coupling 300, or to attach the implement 100 onto the coupling 300 of the handpiece 200. However, unless the outer slider 320 is pulled back, the outer slider 320 is ordinarily biased in the distal direction because of the compression spring 500 disposed between the coupler 310 and the outer slider 320 (i.e., a lock position). Thus, in the lock position, the balls 400 contained within the circumferential holes 390 of the coupler 310 is pushed by the inner contact surface 460 toward the central opening 302 of the coupling 300 and the balls 400 engage with the locking groove 144 of the outer hub 114 for secured attachment of the implement 100 to the handpiece 200. As such, detachment of the implement 100 can be done only when the user pulls the outer slider 320 backwards by one hand and, at the same time, pulls the implement 100 forwards by another hand. This ball-locking construction of the coupling 300, along with the spring 500 and the key and/or pin connection as described above, enables secured and releasable connection of the surgical implement 100 to the handpiece 200. This can also prevent accidental detachment of the implement 100 from the handpiece 200 after they are properly assembled to perform a surgical treatment.

As described above, when the outer hub 114 of the implement 100 is inserted in the axial opening 302 of the coupling 300 for the attachment, the lateral bosses 170 of the inner hub 154 is automatically coupled with the coupling grooves 240 of the rotor 220 with the aid of the guide slopes 250. Thus, while the outer tube member 110 is securely held by the coupling 300, the inner tube member 150 can rotate by the rotor 220 to perform a surgical treatment at the site, such as dissection of body tissue, grinding or removing of bone, and other treatments known in the art.

While this invention has been particularly shown and described with reference to preferred embodiments thereof, it will be understood by those skilled in the art that various changes and modifications in form and details may be made thereto without departing from the spirit and scope of the invention as defined by the appended claims.

What is claimed is:

1. A surgical instrument for performing a surgical treatment to a human or animal body, comprising:
    a surgical implement and a handpiece, wherein the handpiece including an actuator and a coupling for attaching the surgical implement to the handpiece;
    the surgical implement includes an outer tube member with an outer hub and an outer tube extending longitudinally from the outer hub, the outer tube and the outer hub defining a longitudinal bore, the outer hub including a circumferentially extending locking groove that receives at least one locking ball disposed in the coupling and an engaging element disposed at an outer surface of the outer hub for releasable attachment of the outer tube member to the handpiece; and
    an inner tube member including an inner hub and an inner tube extending longitudinally from the inner hub, the inner tube and the inner hub defining a longitudinal bore, the inner tube configured to insert within the longitudinal bore of the outer tube member and including an end effect portion disposed adjacent to a distal end of the inner tube, the inner hub including a connection element radially extending from an outer circumference of the inner hub for releasable connection of the inner tube member to the actuator of the surgical instrument for performing a surgical treatment.

2. The surgical instrument of claim 1, wherein the engaging element of the outer tube member comprises a key for engaging with the coupling of the surgical instrument.

3. The surgical instrument of claim 2, wherein the key has a generally rectangular, circular, or elliptic shape.

4. The surgical instrument of claim 1, wherein the connection element of the inner hub includes a plurality of bosses equidistantly spaced apart and radially extending from the outer circumference of the inner hub.

5. The surgical instrument of claim 4, wherein the bosses of the inner hub each have a generally circular or elliptic configuration.

6. The surgical instrument of claim 1, wherein the outer tube of the outer tube member includes an aperture or window adjacent to a distal end of the tube.

7. The surgical instrument of claim 6, wherein the end effect portion of the inner tube is located at a longitudinal position corresponding to the window of the outer tube for performing a surgical treatment when the inner tube member is assembled within the outer tube member.

8. The surgical instrument of claim 6, wherein the end effect portion of the inner tube comprises a cutting edge for dissecting tissue in association with the window of the outer tube.

9. The surgical instrument of claim 8, wherein the end effect portion of the inner tube includes a distal aperture in fluid communication with the longitudinal bore of the inner tube member.

10. The surgical instrument of claim 6, wherein the end effect portion of the inner tube comprises a surgical burr or grinder.

11. The surgical instrument of claim 1, wherein the inner hub has a cylindrical distal end portion.

12. The surgical instrument of claim 11, wherein the proximal end of the outer hub of the outer tube member includes a stepped bore of cylindrical configuration for receiving the distal end portion of the inner hub in a rotatable manner.

13. The surgical instrument of claim 1, wherein the outer hub of the outer tube member is configured to be coupled with a sealing element of the surgical instrument for providing a sealing effect when the surgical implement is attached to the handpiece of the surgical instrument.

14. The surgical instrument of claim 1, wherein the implement is formed of a metallic material and reusable.

15. The surgical instrument of claim 1, wherein at least some portion of the implement is formed of a plastic material.

16. A surgical instrument for performing a surgical treatment, comprising:
    a surgical implement including an elongate outer tube member and an elongate inner tube member, the outer tube member defining a longitudinal bore, the outer tube member including a distal outer tube and a proximal outer hub, the outer hub having a circumferential locking groove and an engaging element at an outer circumference thereof, the inner tuber member defining another longitudinal bore, the inner tube member including a distal inner tube and a proximal inner hub, the inner hub having a connection element radially extending from an outer circumference of the inner hub, the inner tube of the inner tube member configured to slidably insert within the longitudinal bore of the outer tube member;
    a handpiece including an actuator, and a coupling for attaching the surgical implement to the handpiece;
    wherein the coupling includes a generally cylindrical coupler, the coupler having a longitudinal opening configured to receive a proximal portion of the surgical implement therein and at least one circumferential hole formed through the cylindrical coupler in a radial direction, the coupler further having a counterpart engaging element connectable with the engaging element of the outer hub for attachment of the surgical implement to the handpiece, the coupling further includes at least one locking ball slidably received within the circumferential hole of the coupler, and an outer slider having a longitudinal opening for receiving the coupler therein, the outer slider including a circumferential inner recess and being moveable along the coupler between a lock position where the locking ball is pushed radially by the outer slider for engaging with the circumferential locking groove of the outer hub of the surgical implement for connection of the surgical implement to the coupling of the handpiece and an unlock position where the locking ball is at least partially retrieved into the circumferential recess of the outer slider for allowing detachment of the surgical implement from the coupling of the handpiece; and wherein a distal end of the actuator includes a counterpart connection element for connecting with the connection element of the inner hub of the surgical implement for performing a surgical treatment.

17. The surgical instrument of claim 16, wherein the engaging element of the outer tube member comprises a key disposed at an outer circumference of the outer hub, and the counterpart engaging element of the coupler comprises one or more distal grooves configured to receive the key of the outer tube member therein.

18. The surgical instrument of claim 16, wherein the connection element of the inner hub includes a plurality of bosses equidistantly spaced apart and radially extending from the outer circumference of the inner hub.

19. The surgical instrument of claim 18, wherein the counterpart connection element of the actuator includes a plurality of longitudinally extending coupling grooves for receiving the bosses of the inner hub for the connection of the inner hub with the actuator.

20. The surgical instrument of claim 19, wherein the counterpart connection element of the actuator further includes guide slopes formed adjacent to the coupling grooves of the actuator.

21. The surgical instrument of claim 16, wherein the coupling further includes a spring disposed between the coupler and the outer slider.

22. The surgical instrument of claim 21, wherein the spring is biased to push the outer slider to the lock position.

23. The surgical instrument of claim 16, wherein a proximal end of the outer hub includes a stepped bore and a distal end of the inner hub is slidably received within the stepped bore when the inner tube member is assembled with the outer tube member.

24. The surgical instrument of claim 16, wherein the actuator includes a distal opening for receiving at least a proximal portion of the inner hub therein.

25. The surgical instrument of claim 16, further comprising a suction device configured to draw irrigating fluid and tissue debris via the longitudinal bore of the inner tube member.

* * * * *